US010828161B2

(12) United States Patent
Klotz et al.

(10) Patent No.: US 10,828,161 B2
(45) Date of Patent: Nov. 10, 2020

(54) METHOD OF IMPLANTING JOINT PROSTHESIS WITH INFINITELY POSITIONABLE HEAD

(71) Applicant: DePuy Synthes Products, Inc., Raynham, MA (US)

(72) Inventors: Conrad Klotz, Nappanee, IN (US); Jack Long, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 107 days.

(21) Appl. No.: 15/895,576

(22) Filed: Feb. 13, 2018

(65) Prior Publication Data

US 2018/0177598 A1   Jun. 28, 2018

Related U.S. Application Data

(62) Division of application No. 14/842,229, filed on Sep. 1, 2015, now Pat. No. 9,925,047, which is a division
(Continued)

(51) Int. Cl.
   *A61F 2/30* (2006.01)
   *A61F 2/40* (2006.01)
   *A61F 2/46* (2006.01)

(52) U.S. Cl.
   CPC .............. *A61F 2/30* (2013.01); *A61F 2/4014* (2013.01); *A61F 2/4059* (2013.01);
   (Continued)

(58) Field of Classification Search
   CPC ............... A61F 2/32; A61F 2/00; A61B 17/58
   (Continued)

(56) References Cited

U.S. PATENT DOCUMENTS 4,003,095 A   1/1977   Gristina
4,676,797 A   6/1987   Anapliotis et al.
(Continued)

FOREIGN PATENT DOCUMENTS

DE   4445892 A1   6/1996
DE   19509037 C1   9/1996
(Continued)

OTHER PUBLICATIONS

Australian Search Report in Australian application AU2005247033, dated Apr. 23, 2010 (2 pages).
(Continued)

*Primary Examiner* — Yashita Sharma
(74) *Attorney, Agent, or Firm* — Maginot, Moore & Beck, LLP

(57) ABSTRACT

A method for preparing an articulating component of a joint prosthesis, the prosthesis having an implant engaged within a bone of the joint, the method including inserting a first articulating component into a first insert in the implant within the bone of the joint, determining an angular orientation of the inserted first articulating component relative to the implant within the bone of the joint, positioning a second articulating component within a second insert component, replicating the angular orientation of the first articulating component in the second articulating component positioned within the second insert, fixing the second articulating component to the second insert component at the replicated angular orientation, and mounting the second insert component with the fixed second articulating component to the implant engaged within the bone of the joint.

19 Claims, 4 Drawing Sheets

Related U.S. Application Data of application No. 13/874,025, filed on Apr. 30, 2013, now Pat. No. 9,132,012, which is a division of application No. 11/025,185, filed on Dec. 29, 2004, now Pat. No. 8,444,698.

(52) U.S. Cl.
CPC .. *A61F 2/4603* (2013.01); *A61F 2002/30378* (2013.01); *A61F 2002/30484* (2013.01); *A61F 2002/30538* (2013.01); *A61F 2002/30614* (2013.01); *A61F 2002/30884* (2013.01); *A61F 2002/4029* (2013.01); *A61F 2002/4037* (2013.01); *A61F 2002/4044* (2013.01); *A61F 2220/0025* (2013.01); *A61F 2220/0033* (2013.01); *A61F 2250/0006* (2013.01)

(58) Field of Classification Search
USPC .................. 623/22.11–23.41; 606/91–102
See application file for complete search history.

(56) References Cited

U.S. PATENT DOCUMENTS

| | | |
|---|---|---|
| 4,822,370 A | 4/1989 | Schelhas |
| 5,076,541 A | 12/1991 | Daghe et al. |
| 5,080,685 A | 1/1992 | Bolesky et al. |
| 5,314,479 A | 5/1994 | Rockwood, Jr. et al. |
| 5,358,526 A | 10/1994 | Tornier |
| 5,370,706 A | 12/1994 | Bolesky et al. |
| 5,702,457 A | 12/1997 | Walch et al. |
| 5,725,597 A | 3/1998 | Hwang |
| 5,741,335 A | 4/1998 | Gerber et al. |
| 5,743,898 A | 4/1998 | Bailey et al. |
| 5,910,143 A | 6/1999 | Cripe et al. |
| 5,980,573 A | 11/1999 | Shaffner |
| 6,083,263 A | 7/2000 | Draenert et al. |
| 6,197,062 B1 | 3/2001 | Fenlin |
| 6,203,575 B1 | 3/2001 | Farey |
| 6,206,925 B1 | 3/2001 | Tornier |
| 6,228,120 B1 | 5/2001 | Leonard et al. |
| 6,283,999 B1 | 9/2001 | Rockwood, Jr. |
| 6,328,748 B1 | 12/2001 | Hennig |
| 6,361,566 B1 | 3/2002 | Al-Hafez |
| 6,478,500 B1 | 11/2002 | Farenholtz |
| 6,558,425 B2 | 5/2003 | Rockwood, Jr. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,736,851 B2 | 5/2004 | Maroney et al. |
| 6,736,852 B2 | 5/2004 | Callaway et al. |
| 6,749,637 B1 | 6/2004 | Bahler |
| 6,776,799 B2 | 8/2004 | Ball et al. |
| 6,863,690 B2 | 3/2005 | Ball et al. |
| 6,953,478 B2 | 10/2005 | Bouttens et al. |
| 7,192,449 B1 | 3/2007 | McQueen et al. |
| 7,238,207 B2 | 7/2007 | Blatter et al. |
| 7,431,736 B2 | 10/2008 | Maroney et al. |
| 8,273,093 B2 | 9/2012 | Klotz et al. |
| 8,419,798 B2 | 4/2013 | Ondrla et al. |
| 2001/0041940 A1 | 11/2001 | Pearl |
| 2001/0053935 A1 | 12/2001 | Hartdegen et al. |
| 2002/0016634 A1 | 2/2002 | Maroney et al. |
| 2003/0014112 A1 | 1/2003 | Ralph et al. |
| 2003/0040802 A1 | 2/2003 | Errico et al. |
| 2003/0074079 A1 | 4/2003 | McTighe et al. |
| 2003/0097183 A1 | 5/2003 | Rauscher et al. |
| 2004/0002765 A1 | 1/2004 | Maroney et al. |
| 2004/0010261 A1 | 1/2004 | Hoag et al. |
| 2004/0030400 A1 | 2/2004 | Horber |
| 2004/0064142 A1 | 4/2004 | Ball et al. |
| 2004/0064188 A1 | 4/2004 | Ball et al. |
| 2004/0064189 A1 | 4/2004 | Maroney et al. |
| 2004/0122440 A1 | 6/2004 | Daniels et al. |
| 2004/0167629 A1 | 8/2004 | Geremakis et al. |
| 2005/0113931 A1 | 5/2005 | Horber |
| 2005/0143829 A1 | 6/2005 | Ondrla et al. |
| 2005/0149050 A1 | 7/2005 | Stifter et al. |
| 2005/0187637 A1 | 8/2005 | Karrer et al. |
| 2005/0251263 A1 | 11/2005 | Forrer et al. |
| 2005/0288681 A1 | 12/2005 | Klotz et al. |
| 2006/0142872 A1 | 6/2006 | Klotz et al. |
| 2007/0078519 A1 | 4/2007 | Klotz |
| 2007/0112430 A1 | 5/2007 | Simmen et al. |
| 2012/0323250 A1 | 12/2012 | Klotz et al. |
| 2014/0039508 A1 | 2/2014 | Klotz et al. |

FOREIGN PATENT DOCUMENTS

| | | |
|---|---|---|
| DE | 19951141 A1 | 5/2001 |
| DE | 10123517 C1 | 11/2002 |
| DE | 202005020876 U1 | 10/2006 |
| EP | 0549480 A1 | 6/1993 |
| EP | 0679375 A1 | 11/1995 |
| EP | 0712617 A1 | 5/1996 |
| EP | 0715836 A1 | 6/1996 |
| EP | 0931522 A1 | 7/1999 |
| EP | 1186278 A2 | 3/2002 |
| EP | 1314407 A1 | 5/2003 |
| EP | 1321114 A1 | 6/2003 |
| EP | 1393697 A1 | 3/2004 |
| EP | 1402856 A1 | 3/2004 |
| EP | 1681037 A2 | 7/2006 |
| EP | 1769776 A1 | 4/2007 |
| FR | 2731612 A1 | 9/1996 |
| JP | 2004512922 A1 | 4/2004 |
| WO | 9303688 A1 | 3/1993 |
| WO | 0122905 A1 | 4/2001 |
| WO | 0239932 A1 | 5/2002 |
| WO | 03096870 A2 | 11/2003 |
| WO | 03096939 A1 | 11/2003 |

OTHER PUBLICATIONS

Australian Search Report in Australian application AU2005246996, dated Apr. 27, 2010 (3 pages).
Australian Search Report in Australian application AU2006225167, dated Mar. 22, 2011 (2 pages).
European Search Report in European application EP05257963.8, dated Dec. 20, 2007 (5 pages).
European Search Report in European application EP05257964.6, dated Dec. 20, 2007 (8 pages).
European Search Report in European application EP06255073.6, dated Jan. 5, 2007 (8 pages).
European Search Report in European application EP09162325.6, dated Oct. 2, 2009 (6 pages).
European Search Report in European application EP10178881.8, dated Mar. 10, 2011 (5 pages).
European Search Report in European application EP10178895.8, dated Dec. 14, 2010 (7 pages).
Japanese Office Action in Japanese application JP2005-378997, dated Feb. 9, 2010 (12 pages including translation).
Japanese Office Action in Japanese application JP2006-267228, dated Oct. 5, 2010 (4 pages).
The McElroy Translation Company, English translation of German Patent No. DE 101 23 517 C1, dated Jan. 2006 (20 pages).

METHOD OF IMPLANTING JOINT PROSTHESIS WITH INFINITELY POSITIONABLE HEAD

This is a divisional application of U.S. application Ser. No. 14/842,229 filed Sep. 1, 2015, which issued as U.S. Pat. No. 9,925,047 on Mar. 27, 2018 and which is a divisional application of U.S. application Ser. No. 13/874,025 filed Apr. 30, 2013, which issued as U.S. Pat. No. 9,132,012 on Sep. 15, 2015, which is a divisional of U.S. application Ser. No. 11/025,185 filed Dec. 29, 2004 which issued as U.S. Pat. No. 8,444,698 on May 21, 2013, the entire contents of which are each herein incorporated by reference.

This application is related to U.S. Pat. No. 8,562,686 which issued Oct. 22, 2013.

BACKGROUND OF THE INVENTION

The present invention relates to joint prosthesis, and particularly to prosthesis having an articulating head component. More specifically, the invention relates to a system for achieving infinitely variable positions for the head component relative to a bone engaging portion of the prosthesis.

Repair and replacement of human joints, such as the knee, shoulder, elbow and hip, has become a more and more frequent medical treatment. Longer life spans mean that the joints endure more wear and tear. More sports activities mean greater likelihood of serious joint injuries. Treatment of injuries, wear and disease in human joints has progressed from the use of orthotics to mask the problem, to fusion of the joint, to the use of prostheses to replace the damaged joint component(s).

As the success rate for total or partial joint replacements has increased, so too has the need for modularity and universality in the joint prosthesis. Patient variety means that no single size or configuration of joint prosthesis will suffice. The physical dimensions of a patient's joint components vary, as well as the bio-mechanic relationship between these components. For instance, in a shoulder prosthesis, the relationship between the articulating humeral and glenoid components can be significantly different between patients. These relationships are especially important where only one component of the joint is being replaced and must integrate with the existing natural opposing joint component.

In joint replacement procedures, the proximal end of a bone, such as the humerus, is resected to form a stable platform to receive a joint implant. In some cases, it is discovered after the implant has been fixed within the bone that the resection was inappropriate for the patient's joint. Correction of this problem requires, at a minimum, removal of the implant and implantation of a new implant to fit the resected surface. The availability of a differently sized or configured implant component is very beneficial, and even more important where further resection of the bone is necessary.

For instance, in many shoulder surgeries, only the humeral component is replaced, leaving the glenoid component intact. In this case, it is imperative that the articulating surface of the humeral component match the articulating surface of the glenoid component as perfectly as possible, both statically and dynamically. With a typical humeral prosthesis, version and inclination are adjusted by the geometry of the head of the prosthesis. In other words, certain pre-determined head geometries are available that can be selected for a mating glenoid component. Absent an infinite variety of pre-determined head geometries, the resulting humeral prosthesis can often only achieve a best-fit relationship to the glenoid component of the shoulder joint.

In a typical surgical procedure, a trial component will be used to determine the optimum final component to be fixed to the bone. In most cases, the surgeon is able to make a good selection that fits the joint very well. However, in some cases, the accuracy of the fit cannot be determined until the surgery is completed and the patient has had an opportunity to exercise the repaired joint. Where significantly problems arise, a revision surgery may be necessary to replace an improperly sized or configured joint component. One typical revision surgery requires removal of the entire prosthesis from the bone and replacement with a different prosthesis.

There is a significant need for a joint prosthesis that is both modular and universal. Such a prosthesis would be easily manipulated during the surgery and capable of achieving nearly infinite version and inclination angles. Moreover, an optimum prosthesis would be readily available for modification in a revision surgery without having to remove the entire prosthesis.

SUMMARY OF THE INVENTION

These and other needs of the prior art are met by the present invention in which a joint prosthesis includes a removable component to which the articulating component of the prosthesis is connected. The removable component permits adjustment of the angular orientation of the articulating component so that the joint prosthesis is truly universal.

In one aspect of the invention, the joint prosthesis includes a component configured for engagement within the bone of a patient, such as in a prepared intramedullary canal. The component, or stem, can be configured as a trial stem or as a permanent implant. The proximal end of the stem includes a platform surface which defines features for removably supporting a removable insert component. A fixation element is provided that is used to fix the insert component to the stem. In accordance with one embodiment of the invention, the fixation element is itself removable, although it is capable of achieving substantially permanent, rigid fixation of the insert component to the stem.

The joint prosthesis includes a mating component that has one portion configured to mate with the articulating component and another portion configured to adjustably mate with the insert component. The mating component is also provided with a bore to permit access to the fixation element when the mating component is mated with the insert component, to allow removal of the fixation element and thereby removal of the insert component from the stem with the mating component intact.

In a specific embodiment of the invention, the insert component includes a plate portion and a base portion projecting from the plate portion. The insert component defines a tapered bore therethrough and a fastener bore through the bottom wall of the base portion. The platform surface of the stem defines an insert cavity configured to receive the entire insert component therein. In particular, the insert cavity includes a base recess into which the insert base portion snugly fits, and a plate recess for receiving the plate portion. Preferably, the plate recess is open at one edge of the platform surface to facilitate access to the plate portion of the insert component and ultimately to facilitate dislodgement of the insert component from the insert cavity.

The mating component includes a ball portion that is configured to form a press-fit within the tapered bore of the insert component. The mating component also includes a tapered cylinder configured to mate with a complementary bore defined in the articulating component or head. Both ends of the mating component are therefor configured for a press-fit engagement accomplished by use of a typical impaction tool.

In accordance with a method of the present invention, a joint prosthesis is constructed by placing an insert component into a complementary configured cavity defined in the proximal portion of a bone engaging implant, such as a stem. A fixation element, such as a screw, is used to fix the insert within the stem. A mating component is engaged with the insert component, such as by a press-fit engagement between a tapered bore in the insert and a compressible ball portion on the mating component. An articulating component, such as a femoral head, is then mated with the mating component, such as through a press-fit engagement.

In a further feature of the present invention, a revision procedure includes the step of accessing the fixation element through openings defined in at least the mating component. The fixation element is released from engagement with the stem so that the insert component is no longer fastened thereto. The insert component is then removed, preferably with the mating component and head components fastened undisturbed.

In yet another aspect, the removed insert component with the undisturbed mating component and head component can be transported to a replication instrument. The angular position of at least the mating component may be ascertained relative to a fixed datum using the instrument. That angular position can be conveyed to a new insert and mating component using the instrument. Once the three-dimensional angles have been properly replicated in the new prosthesis components, the mating component can be fixed within the insert component, preferably by impaction. The head component may also be engaged to the mating component, also preferably by impaction. The completed assembly is then conveyed to the stem that has not been removed from the patient's bone. The insert component is placed within the insert cavity in the stem and the fixation element is used to rigidly connect the insert component to the stem with the mating component and head component in their proper anatomic relation to the patient's bone. These steps can be implemented in a true revision surgery to replace an existing prosthesis, or can be carried out during an original joint replacement procedure.

In a further aspect, a method for preparing an articulating component of a joint prosthesis having an implant engaged within a bone of the joint includes inserting a first articulating component into a first insert in the implant within the bone of the joint, determining an angular orientation of the inserted first articulating component relative to the implant within the bone of the joint, positioning a second articulating component within a second insert component, replicating the angular orientation of the first articulating component in the second articulating component positioned within the second insert, fixing the second articulating component to the second insert component at the replicated angular orientation, and mounting the second insert component with the fixed second articulating component to the implant engaged within the bone of the joint.

It is one object of the invention to provide a joint prosthesis that is both modular and universal. This object is achieved by features that permit infinitely variable positioning of a mating joint component relative to a bone engaging portion of the prosthesis.

Another object is to provide a prosthesis that is readily available for modification, whether during initial implantation or during a subsequent revision procedure. One benefit of the invention is that this modification can occur without removing or disturbing the bone engaging component, or stem, of the implant.

These and other objects and benefits of the invention will be appreciated upon consideration of the following written description together with the accompanying figures.

DESCRIPTION OF THE PREFERRED EMBODIMENTS

Figure 1:
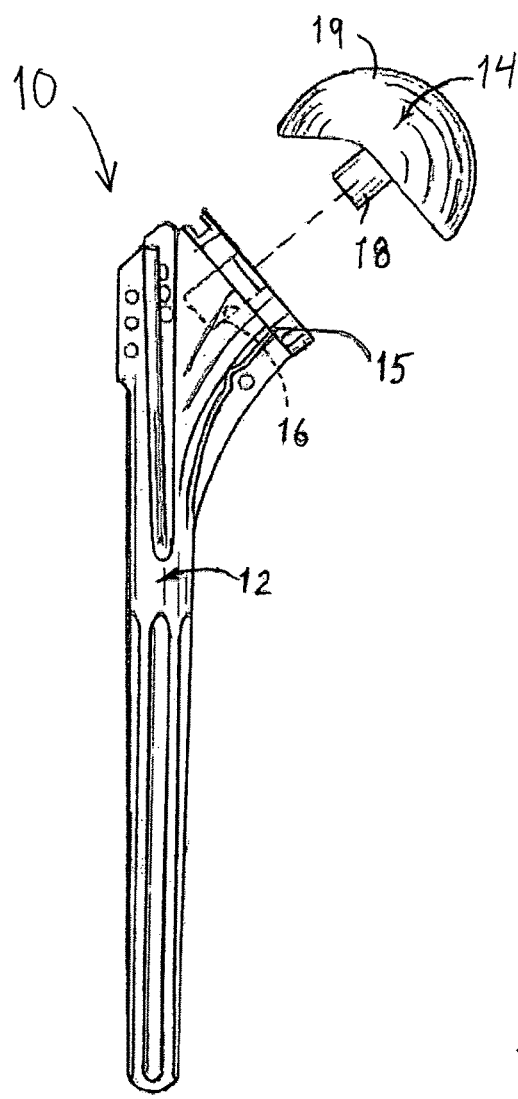
FIG. 1 is a side view of a prior art humeral prosthesis.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a joint prosthesis with an articulating component that must be positioned at a particular angular orientation to replicate and accommodate anatomic features of the patient's joint. In the following description, the prosthesis is identified as a humeral prosthesis for a shoulder implant. It is understood, however, that the principles of this invention can be applied to other prosthesis that include an adjustable component. The present invention is particularly suited for prostheses that are amenable to replacement or adjustment in a revision surgery.

By way of background, a typical joint prosthesis of the prior art is illustrated in FIG. 1. The prosthesis 10 is the humeral component of a shoulder prosthesis that can be implanted in the humerus bone for articulating engagement with the natural glenoid or with a glenoid prosthesis. The prosthesis 10 includes a stem 12 configured to be implanted within the humerus bone in a conventional manner. The stem 12 forms a platform surface 15 that faces the glenoid component of the joint when the prosthesis is in its operative position. The platform surface 15 defines a tapered bore for use in mounting the articulating head component 14. The head component includes a tapered post 18 that can be press-fit or friction-fit within the tapered bore 16 to firmly mount the head component to the stem 12.

The prosthesis 10 can be a modular prosthesis, meaning that a number of stem and head geometries can be provided from which a selection can be made that most closely approximates the natural joint components of the patient. Thus, the angle of the platform surface 15 can be different among stems 12. While all head components 14 will include a generally spherical bearing surface 19, the orientation of this surface relative to the platform surface 15 can be changed. Specifically, the location of the post 18 relative to the bearing surface 19 can be offset from the center of the surface (i.e., an eccentric head). In some cases, the angle of the post can be different between head components 14.

Figure 2:
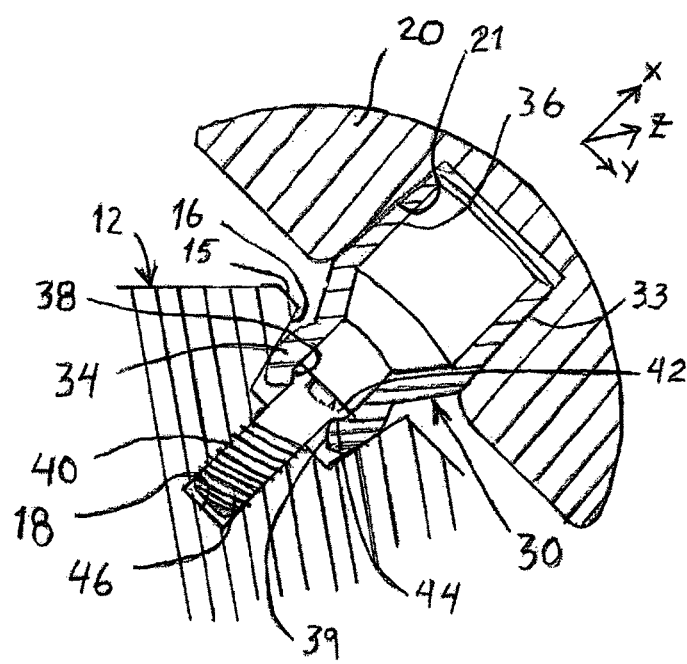
FIG. 2 is an enlarged cross-sectional view of a portion of a joint prosthesis with a mounting element configured for articulating engagement with the stem of the prosthesis to permit angular positioning of a head component in multiple degrees of freedom.

An improved modular prosthesis introduces an articulating mounting element 30 between the stem 12 and a head component 20, as shown in FIG. 2. This mounting element 30 is shown and described in co-pending application Ser. No. 10/748,448 (the '448 Application), entitled JOINT PROSTHESIS WITH INFINITELY POSITIONABLE HEAD, filed on Dec. 30, 2003, and owned by the assignee of the present invention. While the '448 Application provides a more detailed disclosure of the mounting element, which disclosure is incorporated herein by reference, following is a general description to facilitate an understanding of the present invention.

This mounting element 30 of the '448 Application includes a proximal portion 33 that mates with the head component 20. In a specific embodiment, the proximal portion 33 defines a tapered surface that is press-fit or friction-fit within a complementary bore 21 defined in the head component.

The mounting element 30 further includes an articulating portion 34 that is preferably in the form of a spherical ball joint. The articulating portion is sized to achieve a press-fit engagement within a tapered bore 16 of the stem 12 when the portion 34 is pushed sufficiently far into the bore. The spherical shape of the articulating portion 34 allows the mounting element 30 to rotate about three dimensional axes x, y, z. Thus, the mounting element can rotate about its own axis (the x axis), pivot about a version axis (they axis) or pivot about an inclination axis (the z axis).

In addition to the press-fit engagement, a second fixation capability is disclosed in the '448 Application that augments the engagement between the articulating portion 34 and the tapered bore 16. In particular, a machine screw 40 may be provided that includes a threaded portion 46 configured to mate with a threaded bore 18 in the stem 12. The bore 18 is concentrically disposed at the base of the tapered bore 16. The screw 40 is introduced into the threaded bore 18 through the articulating mounting element 30.

As shown in FIG. 2, the mounting element 30 defines a central passageway 36 that extends through the length of element and that is open at its proximal and distal ends. The passageway defines an internal bearing surface 38 at the distal end of the element, or more specifically at the base of the articulating portion 34. The screw includes a head 42 that includes an underside surface 44 that is complementary with the internal bearing surface. These two surfaces form a spherical bearing interface that allows the mounting element 30 to experience its full range of angular motion without interference from the screw 40, even when the screw is loosely threaded into the threaded bore 18. The articulating portion 34 defines a relief 39 at the distal end of the passageway 36 to facilitate this full range of movement of the mounting element.

The passageway 36 in the mounting element allows introduction of the screw 40 through the mounting element and into the threaded bore 18. The screw can be loosely threaded into the bore to permit movement of the mounting element. Once the proper position for the mounting element 30 has been achieved, the screw can be tightened using a tool engaged within the tool recess 43 on the head 42 of the screw. As the screw is tightened, it drives the articulating portion 34 deeper into the angled bore 16, thereby fixing the mounting element against further articulation. The screw thus combines with the friction or press-fit feature to lock the construct.

The mounting element 30 disclosed in the '448 Application represents a significant improvement over the prior art prosthesis 10 in that it greatly simplifies the process of aligning the mounting element, and ultimately the humeral head, at the proper anatomic angle for the patient's shoulder joint. Moreover, the mounting element 30 allows infinite positioning of the humeral head, in lieu of the limited selection of pre-defined angles available with the prosthesis of the prior art.

Even though the mounting element 30 presents a significant advance over the prior prostheses, problems still arise when a revision surgery is indicated. During some primary implant procedures, the surgeon may discover that a different humeral head is needed after the final implant stem has been fixed within the humerus. In some cases, the accuracy of the fit of the prosthetic components cannot be determined until the surgery is completed and the patient has had an opportunity to exercise the repaired joint. Where significant problems arise, a revision surgery may be necessary long after the primary surgery to replace an improperly sized or configured joint component. In most cases, the modular components of the prosthesis cannot be removed without also removing the component, or stem, fixed within the bone. Removal and replacement of an implanted stem is often problematic and runs the risk of creating a revision construct of poor integrity.

Figures 3, 4:
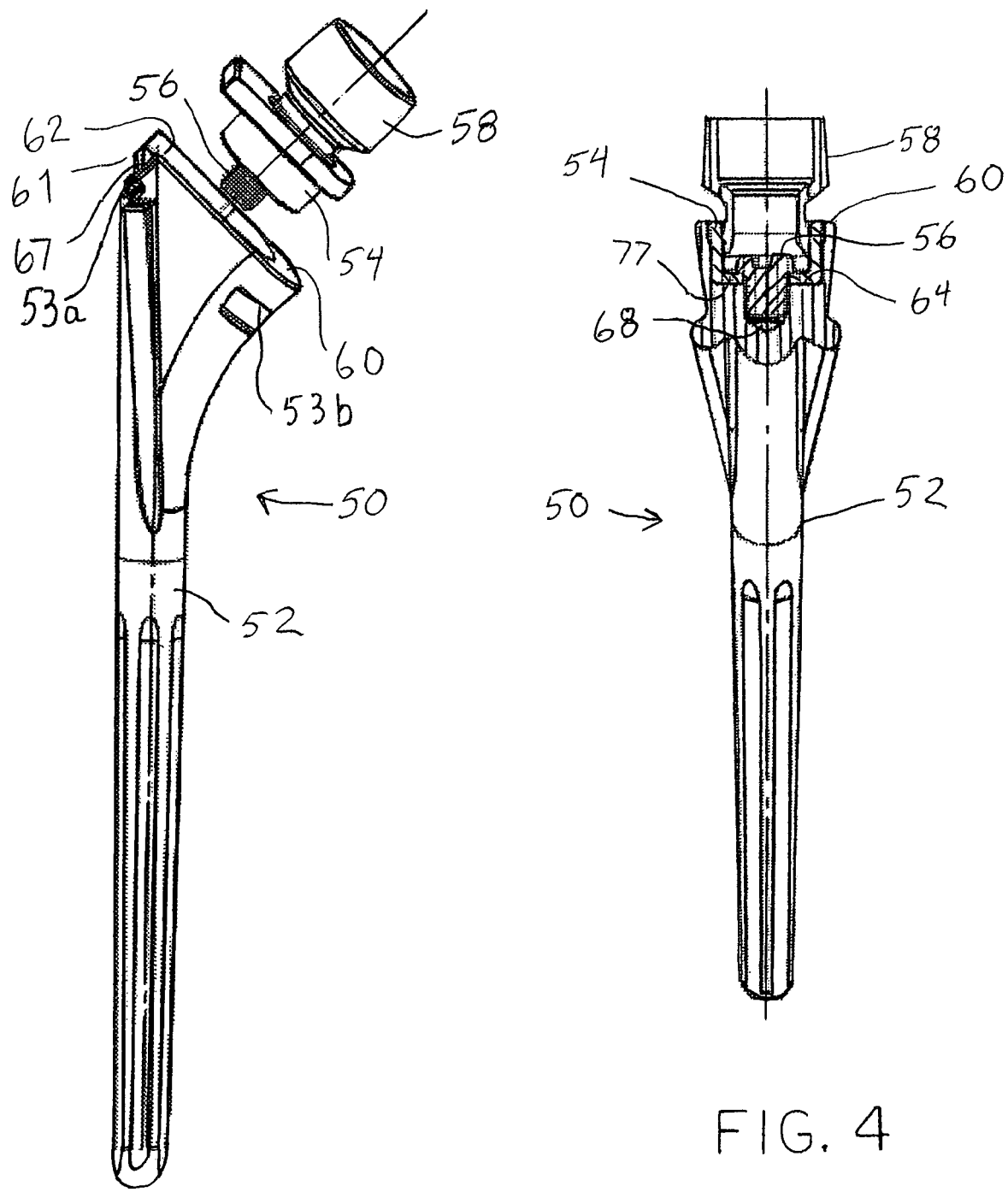
FIG. 3 is a side exploded view of a modular prosthesis in accordance with one embodiment of the present invention that is adapted to facilitate modification or revision of the implant.
FIG. 4 is a front cross-section view of the modular prosthesis shown in FIG. 3 in an assembled configuration.

The present invention addresses the problem of revision surgeries on prosthetic implants by providing an insert component that allows the bone implanted component to remain within the bone. In accordance with one embodiment of the invention, a prosthesis 50 is provided as illustrated in FIGS. 3-4 that includes a stem 52, an insert component 54, a fixation element 56 and a mating component 58. The stem 52 is configured to be implanted within a bone of a patient and may be identical in most respects to prior stems used for similar joint replacement procedures. More particularly, the portion of the stem 52 that is implanted within the prepared intramedullary canal of the humerus may be identical to the prior art stem 12 shown in FIG. 1. As with the prior art stems, the stem 52 includes a platform surface 60 that is aligned toward the mating aspect of the joint, or the glenoid aspect in the case of a shoulder prosthesis.

However, the platform surface 60 of the stem 50 in the present invention takes on different characteristics from the prior art. In particular, the platform surface is configured to receive an insert component 54 and a fixation element 56 operable to rigidly fix the insert component to the stem. The insert component 54 is adapted for engagement with the mating component 58 under conditions that allow adjustment of the angular orientation of that component. The mating component 58 is configured to receive an articulating component, such as the humeral head 20 shown in FIG. 2.

Figure 5:
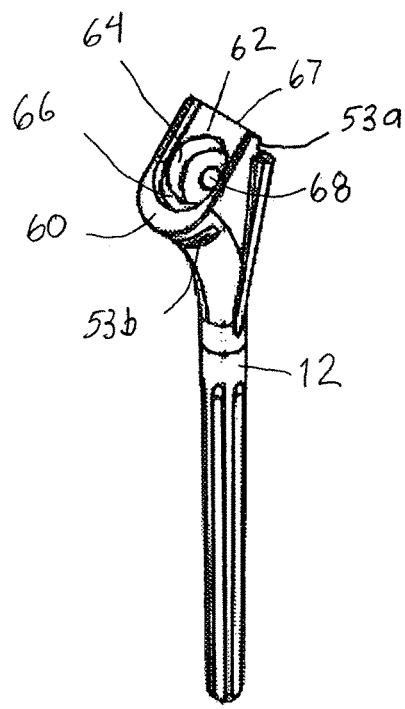
FIG. 5 is a front perspective of a stem component of the modular prosthesis shown in FIGS. 3-4.
Figure 6:
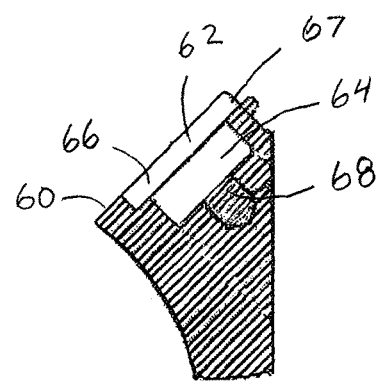
FIG. 6 is an enlarged cross-section view of a portion of the stem depicted in FIG. 5.

Referring to FIGS. 5-6, details of the platform surface 60 of the stem 50 are illustrated. The platform surface defines an insert cavity 62 with a base recess 64 embedded within the stem and a plate recess 66 opening into the platform surface. As shown in FIG. 5, the base recess 64 is preferably cylindrical, for ease of manufacturing and to facilitate placement of the insert component 54 within the insert cavity 62. However, other cross-sectional configurations for the base recess may be acceptable.

The plate recess 66 is generally rectangular with an edge 67 that opens at the superior end 61 of the platform surface 60. The plate recess preferably includes a rounded inboard end to facilitate manufacture of the recess 66. For instance, the base recess 64 can be formed by drilling to a certain depth into the platform surface 60 of the stem 52. The plate recess 66 can be initially formed by drilling concentrically with the base recess, but at a larger diameter and to a shallower depth. The platform surface can then be milled to carve out the open edge 67 of the plate recess.

Figure 7:
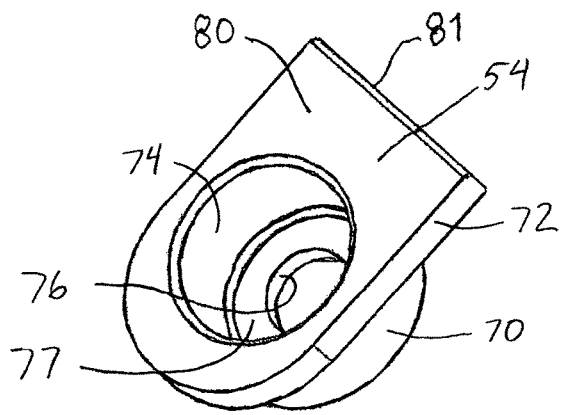
FIG. 7 is a top perspective view of an insert component of the modular prosthesis illustrated in FIGS. 3-4.
Figure 8:
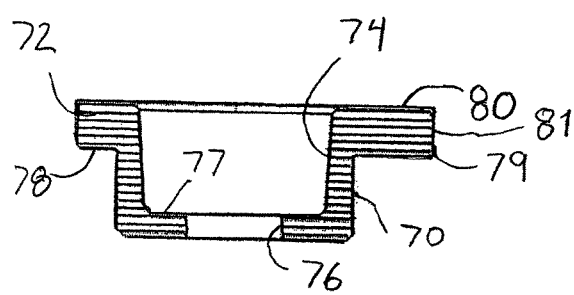
FIG. 8 is a side cross-section view of the insert component shown in FIG. 7.

The insert component 54 is configured to fit snugly within the insert cavity 62, as can be seen from FIGS. 7-8. In particular, the insert component includes a base portion 70 that is configured to be snugly received within the base recess 64. Thus, the cross section of the base portion preferably emulates the cross section of the base recess—i.e., the base portion 70 is cylindrical in the illustrated embodiment. The insert component further includes a plate portion 72 that is also configured to be snugly received within the plate recess 66. As with the base portion, the plate portion 72 follows the configuration of the plate recess 66 so that the base portion is generally rectangular with a rounded inner edge. In the preferred embodiment, the plate portion 54 includes a tab 80 that extends from the cylindrical base portion 70 so that the free end 81 of the tab is accessible at the open edge 67 of the plate recess. Preferably, the free end 81 is substantially coincident with the open edge.

The plate portion 72 defines a lower surface 78 that rests within the plate recess 66. The insert component is preferably sized so that the base portion 70 is slightly offset from the bottom wall 77 of the base recess 64 when the lower surface 78 of the plate portion 72 is situated within the plate recess. The free end 81 of the plate portion 72 includes a lower rounded edge 79 to provide a small access for a removal tool between the insert component and the insert cavity, as discussed in more detail herein.

Figure 9:
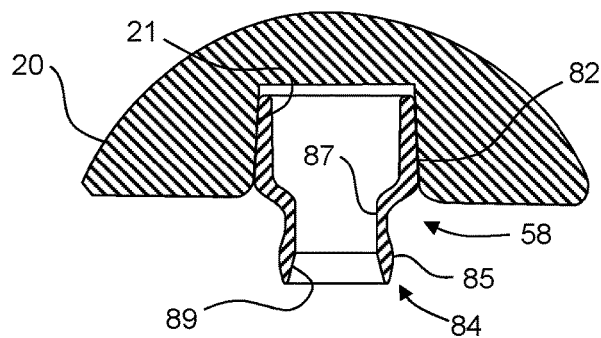
FIG. 9 is a side cross-section view of a mating component of the modular prosthesis shown in FIGS. 3-4.

In one feature of the invention, the insert component 54 defines a tapered bore 74. The tapered bore mates in press-fit engagement with engagement surface 85 of a ball portion 84 of the mating component 58 (FIG. 9). This press-fit engagement accomplishes final fixation of the mating component 58 with the stem 52. This interface may be similar to the press-fit engagement described in the '448 Application incorporated by reference. The mating component preferably includes a tapered cylinder 82 that is configured for press-fit engagement within the complementary bore 21 of the humeral head 20 (also shown in FIG. 2). The mating component includes a central bore 87 that may be configured for a press-fit engagement with a male feature on the humeral head, in lieu of or in addition to the press-fit against the outer surface of the tapered cylinder 82.

Figure 10:
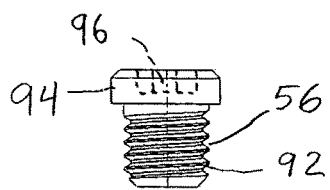
FIG. 10 is a side view of a fixation component of the modular prosthesis shown in FIGS. 3-4.

In order to secure the mating component to the stem 52, a fixation element 56 is provided that fixes the insert component 54 to the stem. In the preferred embodiment, the insert cavity 62 of the stem defines a threaded bore 68 in the base recess 64. The fixation element 56 constitutes a screw, as shown in FIG. 10, with a threaded stem 92 adapted to engage the threaded bore 68. The head 94 of the screw preferably includes a hex recess 96 for receiving a hex driving tool of known design. The insert component 54 includes a fastener bore 76 through the bottom wall 77 of the component to receive the fastener therethrough. Thus, the insert component is fixed to the stem 52 using the fixation element or screw 56, as shown in FIG. 4. The ball portion 84 of the mating component 58 preferably defines a flared opening 89 to prevent contact between the mating component and the head of the screw when the mating component 58 is impacted within the tapered bore 74.

The fixation element 56 represents one beneficial feature of the prosthesis 50 of the present invention. Specifically, the fixation element allows removal of the insert component 54 from the prosthesis stem 52 at any time, including when the mating component 56 is in solid engagement with the insert component. This feature facilitates revision of the articulating component, or humeral head, at any time by simply unscrewing the fixation element 56 from the threaded bore 68 in the stem. When the fixation element 56 is removed, the insert component 54 can be readily extracted from the insert cavity 62 in the stem. Preferably, a tool can be pressed between the rounded edge 79 of the tab portion 80 of the insert component and the platform surface 60 of the stem to help dislodge the insert without contacting the mating component 58. Once removed, the insert component and mating component can serve as a trial component that is replicated in a final prosthesis.

Whether as a final implant or a trial implant, when the mating portion 58 is installed in the tapered bore 74, the ball portion 84 may be initially loosely situated within the bore 74 so that the angular orientation of the mating component 58 can be adjusted. This adjustment may occur with the articulating head component 20 mounted on the mating component. Once the proper angles have been determined, the mating component can be fixed within the tapered bore by impaction in a known manner, and the humeral head can be added in a similar fashion. It can be appreciated that since the mating component is engaging a removable insert component 54 the impaction steps may occur apart from the implant stem 52. Thus, the impaction of the mating component into the insert component, and the impaction of the articulating head onto the mating component can occur on a fixture. Rigid fixation of the final implant may be accomplished through means other than impaction, but this fixation may still occur apart from the stem implanted within the patient's bone.

Preferably, the adjustment of the angular position of the mating component for use in a final prosthesis can occur using a replication instrument, such as the instrument disclosed in co-pending application Ser. No. 10/879,261 (the '261 Application), entitled INSTRUMENTATION FOR RECORDING AND REPLICATING ORTHOPAEDIC IMPLANT ORIENTATION, owned by the assignee of the present invention, the disclosure of which is incorporated herein by reference.

Figure 11:
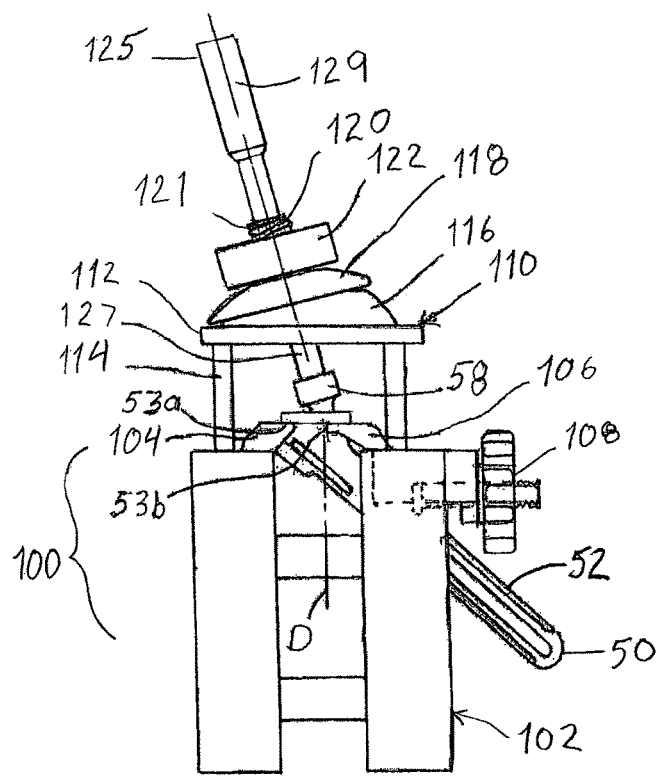
FIG. 11 is a side view of a replication instrument for use in replicating the orientation of the mating component of the prosthesis shown in FIGS. 3-4.

While details of the instrument are found in the '261 Application, following is a general description of the instrument 100 as depicted in FIG. 11. In particular, the instrument includes a base assembly 102 that carries a stationary clamp element 104 and a movable clamp element 106. An adjustment mechanism 108 may be manually operated to move the movable clamp element toward the stationary element 104. The neck of the prosthesis stem 52 is provided with positioning grooves 53a and 53b. The superior groove 53a accepts the fixed clamp element 104, while a pair of inferior grooves 53b are configured to mate with the movable clamp element 106. When the neck of the stem is engaged by the clamp elements 104, 106, a fixed datum D is established that is perpendicular to the platform surface 60. The spatial angular orientation of the mating component 58 is gauged relative to this datum. The base assembly 102 thus establishes a fixed spatial position for this datum that can be used to replicate the angles of the mating component.

To achieve this replication, the instrument 100 further includes a replication fixture 110 that is mounted on the base assembly 102. The fixture includes a platform 112 with legs 114 that are supported on the base assembly. The platform 110 includes an annular dome 116 which supports a spherical washer 118 on one surface and a cannulated guide member 120 on the opposite surface. The guide member includes a hollow stem portion 121 that passes through the dome 116 and washer 118. The stem portion 121 is threaded to receive a locking nut 122 to fix the angular orientation of the guide member 120 relative to the datum D.

As explained in more detail in the '261 Application, the guide member 120 cannula allows passage of an alignment tool 125, and more particularly the guide shaft 127 of the tool. The distal end of the guide shaft is sized to fit snugly within the bore 87 of the tapered cylinder 58. When the guide shaft 127 is situated within the cylinder of the mating component used as part of the trial assembly, the guide member 120 and spherical washer 118 assume a corresponding spatial angle relative to the dome 116. At this point in the method, the locking nut is tightened, thereby fixing the three-dimensional angular position of the guide member 120. The replication fixture 110 is then removed and stem 52 is released from the base assembly. A final humeral prosthesis configured as the prosthesis 50 shown in FIGS. 3-4 may then clamped within the base assembly with a final mating element 58 loosely engaged within the tapered bore 74 of a final insert component 54. The alignment tool is reinserted into the guide member and the guide shaft is engaged with the mating component to replicate the angular orientation of the trial component. The alignment tool 125 is configured with an impaction end 129 that can be struck with a mallet to impact the mating element into the insert component to form the replicated final construct. Once the humeral head is impacted onto the mating component, the insert component can be positioned within the insert cavity 62 of a stem 52 implanted within the prepared intramedullary canal of the patient's bone. The insert component is then fixed in place using the fixation element 56.

Figure 12:
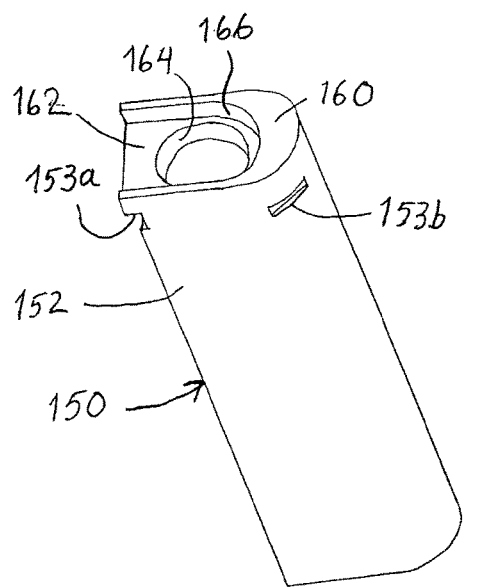
FIG. 12 is a perspective view of a dummy stem for use in the replication instrument shown in FIG. 11.

As shown in FIG. 11, the replication instrument 100 engages a prosthesis 50 that can be configured as a final or a trial prosthesis. However, for the purposes of providing a baseline for replicating the angular orientation of the articulating components of the joint, an entire bone implant is not necessary. Thus, in an alternative method for replicating the necessary angles, a dummy prosthesis 150 is provided as shown in FIG. 12. The dummy prosthesis 150 meticulously emulates the proximal portion of the trial or final prosthesis 50 to provide the proper alignment of the datum line D (FIG. 11). Thus, the dummy prosthesis includes a truncated stem 152 that includes positioning grooves 153a, 153b that are identical to the grooves 53a, 53b described above. These dummy grooves are engaged by the clamp elements 104, 106, in the manner described above. The proximal end of the dummy prosthesis 150 defines an insert cavity 162 with a base recess 164 and plate recess 166, all configured to receive the insert component 54.

The dummy prosthesis 150 functions the same as a final or trial prosthesis when mounted within the replication instrument 100. However, the dummy stem 152 does not require the features found on an implantable stem, since the dummy prosthesis 150 is not configured for implantation within the patient's bone. Preferably, the stem 152 is about ⅓ the length of the final prosthesis stem so that the dummy prosthesis is easy to manipulate and fix within the replication instrument.

As explained above, the illustrated embodiment provides a prosthesis for the humeral aspect of the shoulder joint. Thus, the prosthesis 50 and its components are appropriately dimensioned for implantation within the humerus bone of the patient. In a specific embodiment, the base portion 70 of the insert component 54 has a diameter of 0.5 inches and a height of 0.183 inches to fit within a comparably dimensioned base recess 64. The plate portion 72 has a width of 0.525 inches, a thickness of 0.1 inches, and an overall length of 0.752 inches to fit within a plate recess 66 of the same dimensions. The threaded stem 92 of the fixation screw 56 has a length of 0.197 inches to pass through the bottom wall 77 of the insert portion and into a bore 76 threaded to a depth of 0.175 inches. Preferably, the plate portion 72 of the insert is sized to sit substantially flush with the platform surface 60 of the prosthesis 50

Furthermore, the components of the prosthesis are formed of acceptable medical grade materials appropriate for the particular function being served by the components. For instance, the stem is formed of a material appropriate for implantation within a prepared intramedullary canal. The insert component and mating component are formed of a biocompatible material appropriate for the mating engagement between these components.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, the mating interface between the insert component and the mating component can be reversed. Specifically, the tapered bore may be incorporated into the mating component, while the ball portion projects from the insert component. The same modification can be made to the mating interface between the humeral head and the mating portion.

In the preferred embodiment, the fixation element is a machine screw; however, other forms of fixation or fastening are contemplated. For instance, rather than a screw that requires multiple turns for complete fixation, the element can incorporate a rotating locking cam or bayonet mount arrangement. As a further alternative, the fixation element can incorporate a press-in feature in which the element is pressed into the bore and locks in place, such as a spring clip construction. The fixation element must be capable of achieving a rigid attachment of the insert component to the stem. Moreover, it is preferred that the fixation element be capable of removal without disturbing or damaging the implanted stem.

In accordance with the preferred embodiment of the invention, the insert component is removable to facilitate revision or replacement of the angularly adjustable components. In one specific application, the insert component is implemented solely as a trial implant wherein the insert component is removably fixed to the stem to permit positioning of the mating component and femoral head in a proper anatomic orientation. With the mating component locked in its acceptable position, the insert component can be removed and placed within a replication instrument. The orientation of the mating component may then be replicated in a final prosthesis that does not include the insert component.

The present invention provides advantages even if the insert component is permanently fixed to the stem. Where the final implant includes the insert component, the insert component may be permanently fixed to the implanted stem with an appropriate fixation element. This variation still takes advantage of the ability to establish a final angular orientation of the mating component outside the surgical site.

What is claimed is:

1. A method for preparing an articulating component of a joint prosthesis, the prosthesis having an implant engaged within a bone of the joint, the method comprising:
   inserting a first articulating component into a first insert component in the implant within the bone of the joint;
   determining an angular orientation of the inserted first articulating component relative to the implant within the bone of the joint;
   positioning a second articulating component within a selected one of the first insert component and a second insert component;
   replicating, with the second articulating component within the selected one of the first and second insert component, the determined angular orientation of the first articulating component in the first insert component;
   fixing the second articulating component to the selected one of the first and second insert component at the replicated angular orientation; and
   mounting the selected one of the first and second insert component with the fixed second articulating component to the implant engaged within the bone of the joint by
      inserting a first insert portion of the selected one of the first and second insert component into a first cavity portion of the implant, and
      inserting a second insert portion of the selected one of the first and second insert component into a second cavity portion of the implant, wherein the first insert portion, the first cavity portion, the second insert portion, and the second cavity portion are configured such that the selected one of the first and second insert can only be mounted in a single predetermined orientation with respect to the implant.

2. The method for preparing an articulating component of a joint prosthesis of claim 1, further comprising fixing the mounted selected one of the first and second insert component to the implant using a fastener.

3. The method for preparing an articulating component of a joint prosthesis of claim 1, wherein the selected one of the first and second insert component is the first insert component.

4. The method for preparing an articulating component of a joint prosthesis of claim 1, wherein fixing the second articulating component includes impacting the selected one of the first and second insert component and the second articulating component together.

5. The method of claim 1, wherein replicating comprises:
   mounting the selected one of the first and second insert component to a proximal portion of a dummy implant of a replication instrument, the dummy implant configured to emulate a proximal portion of the implant within the bone of the joint; and
   using the replication instrument to replicate, with the second articulating component within the selected one of the first and second insert component, the determined angular orientation of the first articulating component relative to the first insert component.

6. The method of claim 5, wherein determining comprises:
   mounting the first insert component to the proximal portion of the dummy implant; and
   determining the angular orientation of the articulating component relative to the dummy implant.

7. The method of claim 6, wherein replicating further comprises:
   inserting a ball portion of a mating component into a tapered bore of the insert; and
   engaging a tapered cylinder portion of the mating component with the new articulating component.

8. The method of claim 7, wherein replicating further comprises:
   press fitting the ball portion within the tapered bore.

9. The method of claim 8, wherein replicating further comprises:
   impacting the press fit ball portion within the tapered bore using an alignment tool of the replication instrument.

10. A method for preparing an articulating component of a joint prosthesis, the prosthesis having an implant engaged within a bone of the joint, the method comprising:
    inserting a first articulating component into a first insert component in the implant within the bone of the joint;
    determining an angular orientation of the inserted first articulating component relative to the implant within the bone of the joint;
    positioning a second articulating component within a selected one of the first insert component and a second insert component;
    replicating, with the second articulating component within the selected one of the first and second insert component, the determined angular orientation of the first articulating component in the first insert component;
    fixing the second articulating component to the selected one of the first and second insert component at the replicated angular orientation; and
    mounting the selected one of the first and second insert component with the fixed second articulating component to the implant engaged within the bone of the joint by
       inserting a cylindrical portion of the selected one of the first and second insert component into a cavity of the implant through a platform plane defined by a platform surface of the implant, wherein the selected one of the first and second insert component is configured to mate with the implant in a rotationally keyed configuration which rotationally fixes the selected one of the first and second insert component in the cavity at a predetermined rotational angle.

11. The method of claim 10, wherein mounting further comprises:
    mating a projecting portion of the selected one of the first and second insert component with a recess in the implant, the recess having a first opening portion that opens to the platform surface and a second opening portion that opens to a side of the implant extending away from the platform surface.

12. The method of claim 10, further comprising fixing the mounted selected one of the first and second insert component to the implant using a fastener.

13. The method of claim 10, wherein the selected one of the first and second insert component is the first insert component.

14. The method of claim 10, wherein fixing the second articulating component includes impacting the selected one of the first and second insert component and the second articulating component together.

15. The method of claim 10, wherein replicating comprises:
mounting the selected one of the first and second insert component to a proximal portion of a dummy implant of a replication instrument, the dummy implant configured to emulate a proximal portion of the implant within the bone of the joint; and
using the replication instrument to replicate, with the second articulating component within the selected one of the first and second insert component, the determined angular orientation of the first articulating component relative to the first insert component.

16. The method of claim 15, wherein determining comprises:
mounting the first insert component to the proximal portion of the dummy implant; and
determining the angular orientation of the articulating component relative to the dummy implant.

17. The method of claim 16, wherein replicating further comprises:
inserting a ball portion of a mating component into a tapered bore of the insert; and
engaging a tapered cylinder portion of the mating component with the new articulating component.

18. The method of claim 17, wherein replicating further comprises:
press fitting the ball portion within the tapered bore.

19. The method of claim 18, wherein replicating further comprises:
impacting the press fit ball portion within the tapered bore using an alignment tool of the replication instrument.

\* \* \* \* \*